(12) United States Patent
Zhang et al.

(10) Patent No.: US 12,210,005 B2
(45) Date of Patent: Jan. 28, 2025

(54) DIAGNOSTIC METHOD AND SYSTEM FOR DRIP IRRIGATION COTTON WITH NITROGEN NUTRIENT DEFICIT

(71) Applicant: Shihezi University, Shihezi (CN)

(72) Inventors: Ze Zhang, Shihezi (CN); Xiangyu Chen, Shihezi (CN); Xin Lv, Shihezi (CN); Qiang Zhang, Shihezi (CN); Lulu Ma, Shihezi (CN); Yiru Ma, Shihezi (CN)

( * ) Notice: Subject to any disclaimer, the term of this patent is extended or adjusted under 35 U.S.C. 154(b) by 0 days.

(21) Appl. No.: 17/782,134

(22) PCT Filed: Dec. 21, 2021

(86) PCT No.: PCT/CN2021/140107
§ 371 (c)(1),
(2) Date: Jun. 2, 2022

(87) PCT Pub. No.: WO2022/222522
PCT Pub. Date: Oct. 27, 2022

(65) Prior Publication Data
US 2024/0159725 A1    May 16, 2024

(30) Foreign Application Priority Data
Apr. 20, 2021   (CN) .......................... 202110425638.X

(51) Int. Cl.
*G01N 21/55*   (2014.01)
*G01N 33/00*   (2006.01)

(52) U.S. Cl.
CPC ......... *G01N 33/0098* (2013.01); *G01N 21/55* (2013.01)

(58) Field of Classification Search
CPC .............. G01N 33/0098; G01N 21/55; G01N 2201/0221; G01N 21/31; G01N 21/84; G01N 2021/8466; G01N 21/25; A01C 21/007
See application file for complete search history.

(56) References Cited

U.S. PATENT DOCUMENTS

| | | | |
|---|---|---|---|
| 6,855,933 B2 * | 2/2005 | Stone ....................... | G01J 3/427 250/341.1 |
| 2004/0261191 A1 * | 12/2004 | Yang .................... | D06M 15/667 8/115.51 |
| 2005/0254049 A1 * | 11/2005 | Zhao ..................... | G01N 21/211 356/369 |

* cited by examiner

*Primary Examiner* — Abdullahi Nur

(57) ABSTRACT

The invention relates to a diagnostic method and system for drip irrigation cotton with nitrogen nutrient deficit. First, the sensitive leaf layer of cotton is determined according to the growth stage of cotton, and the spectral reflectance and biomass of each functional leaf in the sensitive leaf layer are collected to calculate average spectral reflectance of the sensitive leaf layer and the maximum leaf biomass. Then, the critical nitrogen concentration was calculated according to the maximum leaf biomass. Finally, the nitrogen nutrition index of cotton is calculated according to the nitrogen concentration and the critical nitrogen concentration. The nitrogen nutrition index is used to characterize the abundance and deficiency of nitrogen nutrition in cotton, so as to determine the abundance and deficiency of nitrogen nutrition in cotton, which can reduce the calculation amount of nitrogen nutrition index, diagnose the abundance and deficiency of nitrogen nutrition in drip irrigation cotton.

10 Claims, 7 Drawing Sheets

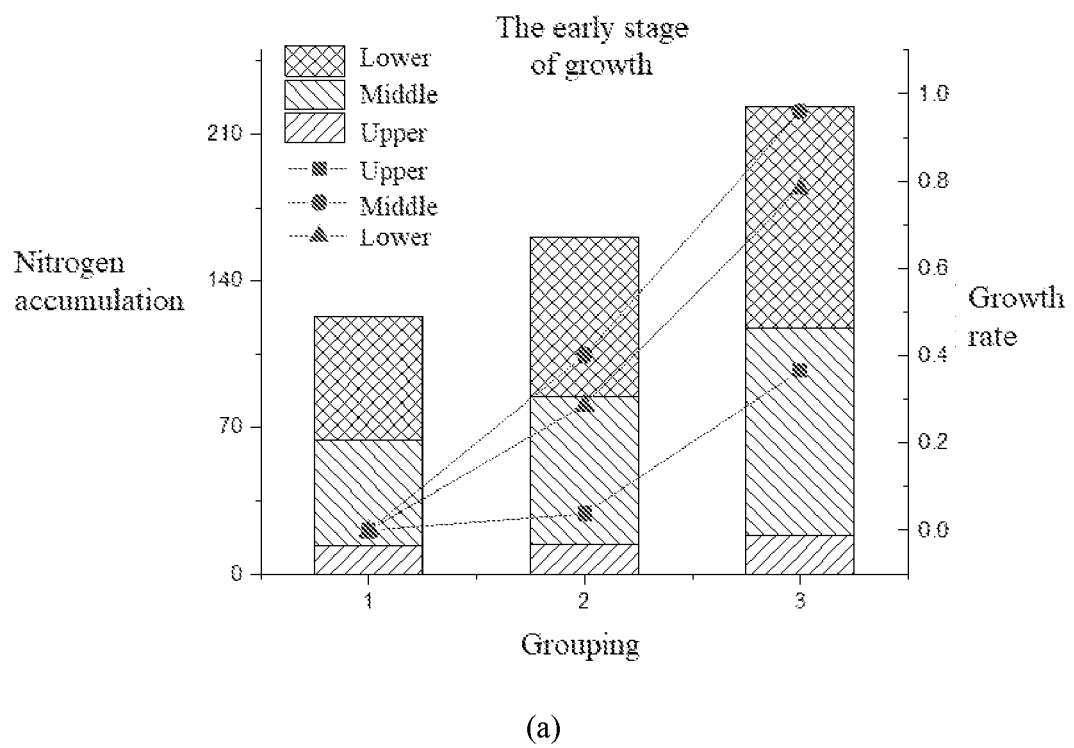
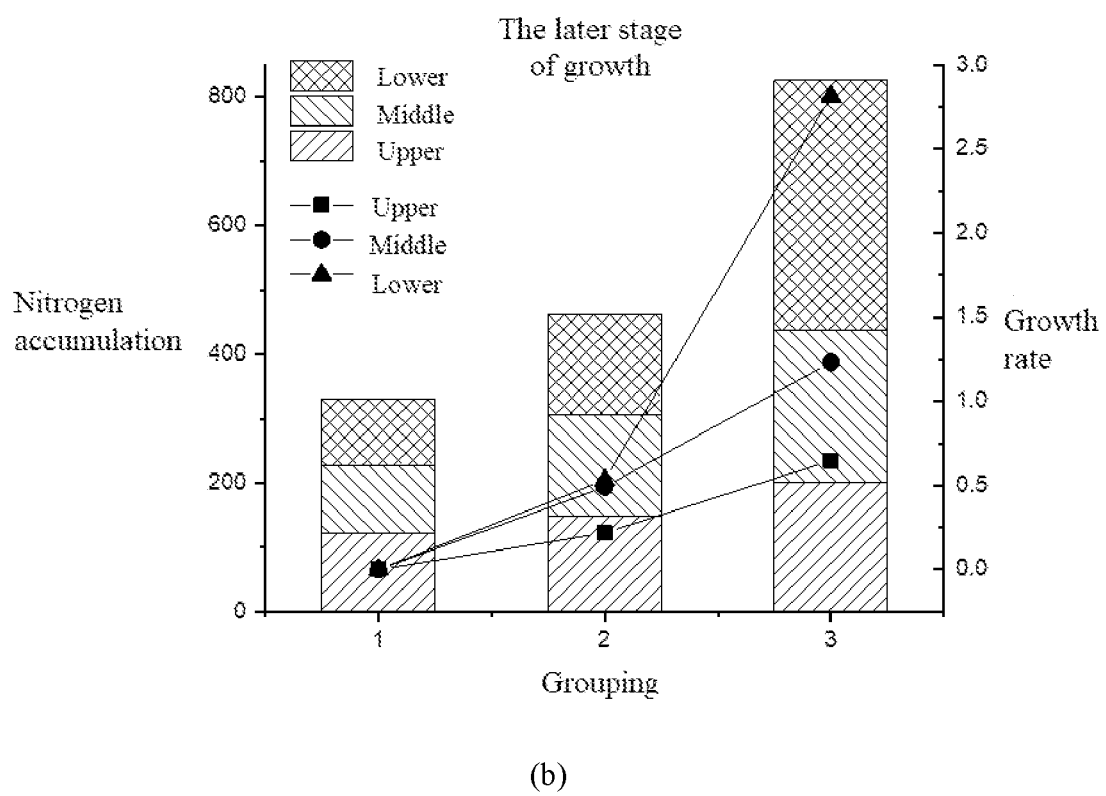
FIG. 3

Collect the spectral reflectance and nitrogen concentration of each functional leaf in the sensitive leaf layer of several plants of the cotton, and calculate the average spectral reflectance of the cotton according to the spectral reflectance of each functional leaf, calculate the average nitrogen concentration of the cotton according to the nitrogen concentration of each functional leaf;

↓ S31

According to the average value of spectral reflectance and the average value of nitrogen concentration, use SPA and RF to screen multiple sensitive bands;

↓ S32

The central wavelength of the spectral index is optimized by using the sensitive band to obtain the optimized spectral index.

DIAGNOSTIC METHOD AND SYSTEM FOR DRIP IRRIGATION COTTON WITH NITROGEN NUTRIENT DEFICIT

1. TECHNICAL FIELD

The invention relates to the technical field of nitrogen nutrition diagnosis, in particular to a diagnostic method and system for drip irrigation cotton with nitrogen nutrient deficit.

2. BACKGROUND ART

Nitrogen, as the main nutrient element for crop growth and development, yield and quality, plays a key role in crop growth and development. However, unreasonable nitrogen fertilizer application will not only reduce fertilizer utilization efficiency and cause fertilizer waste, but also bring serious environmental pollution problems. Therefore, it is of great significance to grasp the nitrogen nutrition of cotton plants in the process of growth in real time, and to construct an efficient and scientific nitrogen monitoring and diagnosis method, which is of great significance to determine the reasonable amount of nitrogen application and improve the efficiency of nitrogen fertilizer use.

Studies by related scholars have found that crop canopy has obvious vertical heterogeneity characteristics. When crops are under nitrogen stress, nitrogen nutrition in old leaves in the lower part of the canopy will be transferred to new leaves, and the lower leaves will turn yellow and senescent and gradually expand to the upper leaves. Since traditional remote sensing spectral observations usually use vertical observations, the top of the canopy has an absolute advantage in the spectral contribution rate, and it is difficult to obtain the symptom information of early nitrogen deficiency in the middle and lower leaves in time. The delay of nutrition diagnosis affects the timeliness of optimal supply of nitrogen fertilizer for crops. Therefore, there is an urgent need for methods to accurately diagnose early nitrogen deficiency in crops.

3. SUMMARY OF THE INVENTION

The purpose of the present invention is to provide a diagnostic method and system for drip irrigation cotton with nitrogen nutrient deficit, which can accurately and quickly diagnose the nitrogen nutrient deficiency of drip irrigation cotton and meet the timeliness requirements of precision agricultural production.

For achieving the above object, the present invention provides the following scheme:

A diagnostic method for drip irrigation cotton with nitrogen nutrient deficit, wherein the diagnostic method comprises the following steps:

The sensitive leaf layer of cotton is determined according to the growth stage of cotton;

The spectral reflectance and biomass of each functional leaf in the sensitive leaf layer are collected to calculate average spectral reflectance of the sensitive leaf layer and the maximum leaf biomass;

The optimized spectral index value was calculated according to the average spectral reflectance, the nitrogen concentration was calculated according to the optimized spectral index value;

The critical nitrogen concentration was calculated according to the maximum leaf biomass;

The nitrogen nutrition index of cotton is calculated according to the nitrogen concentration and the critical nitrogen concentration. The nitrogen nutrition index is used to characterize the abundance and deficiency of nitrogen nutrition in cotton.

A system for drip irrigation cotton with nitrogen nutrient deficit, wherein the diagnosis system comprises:

A sensitive leaf layer determination module, used for determining the sensitive leaf layer of the cotton according to the growth stage of the cotton;

A collection module, configured to collect the spectral reflectance and biomass of each functional leaf in the sensitive leaf layer, and calculate the average spectral reflectance and the maximum leaf biomass of the sensitive leaf layer;

A nitrogen concentration calculation module, configured to calculate an optimized spectral index value according to the average spectral reflectance, and to calculate a nitrogen concentration according to the optimized spectral index value;

A critical nitrogen concentration calculation module, configured to calculate the critical nitrogen concentration according to the maximum leaf biomass;

A nitrogen nutrient index calculation module, used for calculating the nitrogen nutrient index of the cotton according to the nitrogen concentration and the critical nitrogen concentration; the nitrogen nutrient index is used to characterize the nitrogen nutrient abundance of the cotton.

According to the specific embodiments provided by the present invention, the present invention discloses the following technical effects:

The invention relates to a diagnostic method and system for drip irrigation cotton with nitrogen nutrient deficit. First, the sensitive leaf layer of cotton is determined according to the growth stage of cotton, and the spectral reflectance and biomass of each functional leaf in the sensitive leaf layer are collected to calculate average spectral reflectance of the sensitive leaf layer and the maximum leaf biomass. Then, the optimized spectral index value was calculated according to the average spectral reflectance, the nitrogen concentration was calculated according to the optimized spectral index value, and the critical nitrogen concentration was calculated according to the maximum leaf biomass. Finally, the nitrogen nutrition index of cotton is calculated according to the nitrogen concentration and the critical nitrogen concentration. The nitrogen nutrition index is used to characterize the abundance and deficiency of nitrogen nutrition in cotton, and then the sensitive leaf layer is pre-determined, and the spectral data of the sensitive leaf layer is collected to calculate the nitrogen nutrition index, so as to determine the abundance and deficiency of nitrogen nutrition in cotton, which can reduce the calculation amount of nitrogen nutrition index, and solve the problem that the canopy reflectance ratio is too high and the diagnosis delay when using hyperspectral to quickly detect the nitrogen nutrient abundance of cotton. It can accurately diagnose the nitrogen nutrient abundance of drip irrigation cotton and meet the timeliness requirements of precision agricultural production.

4. BRIEF DESCRIPTION OF ACCOMPANY DRAWING

In order to more clearly illustrate the embodiments of the present invention or the technical solutions in the prior art, the accompanying drawings required in the embodiments will be briefly introduced below. Obviously, the drawings in the following description are only some of the present invention. In the embodiments, for those of ordinary skill in the art, other drawings can also be obtained according to these drawings without any creative effort.

FIG. 3 is a schematic diagram of the distribution of nitrogen accumulation in each layer of cotton leaves under different nitrogen application treatments provided in Embodiment 1 of the present invention.

FIG. 5 is a method flowchart for optimizing the central wavelength of a spectral index to obtain an optimized spectral index according to Embodiment 1 of the present invention.

5. SPECIFIC EMBODIMENT OF THE INVENTION

The technical solutions in the embodiments of the present invention will be clearly and completely described below with reference to the accompanying drawings in the embodiments of the present invention. Obviously, the described embodiments are only a part of the embodiments of the present invention, rather than all the embodiments. Based on the embodiments of the present invention, all other embodiments obtained by those of ordinary skill in the art without creative efforts shall fall within the protection scope of the present invention.

The purpose of the present invention is to provide a diagnostic method and system for drip irrigation cotton with nitrogen nutrient deficit, which is used to solve the problems that the reflectance ratio of the cotton canopy is too high and the diagnosis is delayed when using hyperspectral to quickly detect the nitrogen abundance of cotton. It can accurately and quickly diagnose the abundance and deficiency of nitrogen nutrition in drip irrigation cotton, and meet the timeliness requirements of precision agricultural production.

In order to make the above objects, features and advantages of the present invention more clearly understood, the present invention will be described in further detail below with reference to the accompanying drawings and specific embodiments.

Embodiment 1

Figure 1:
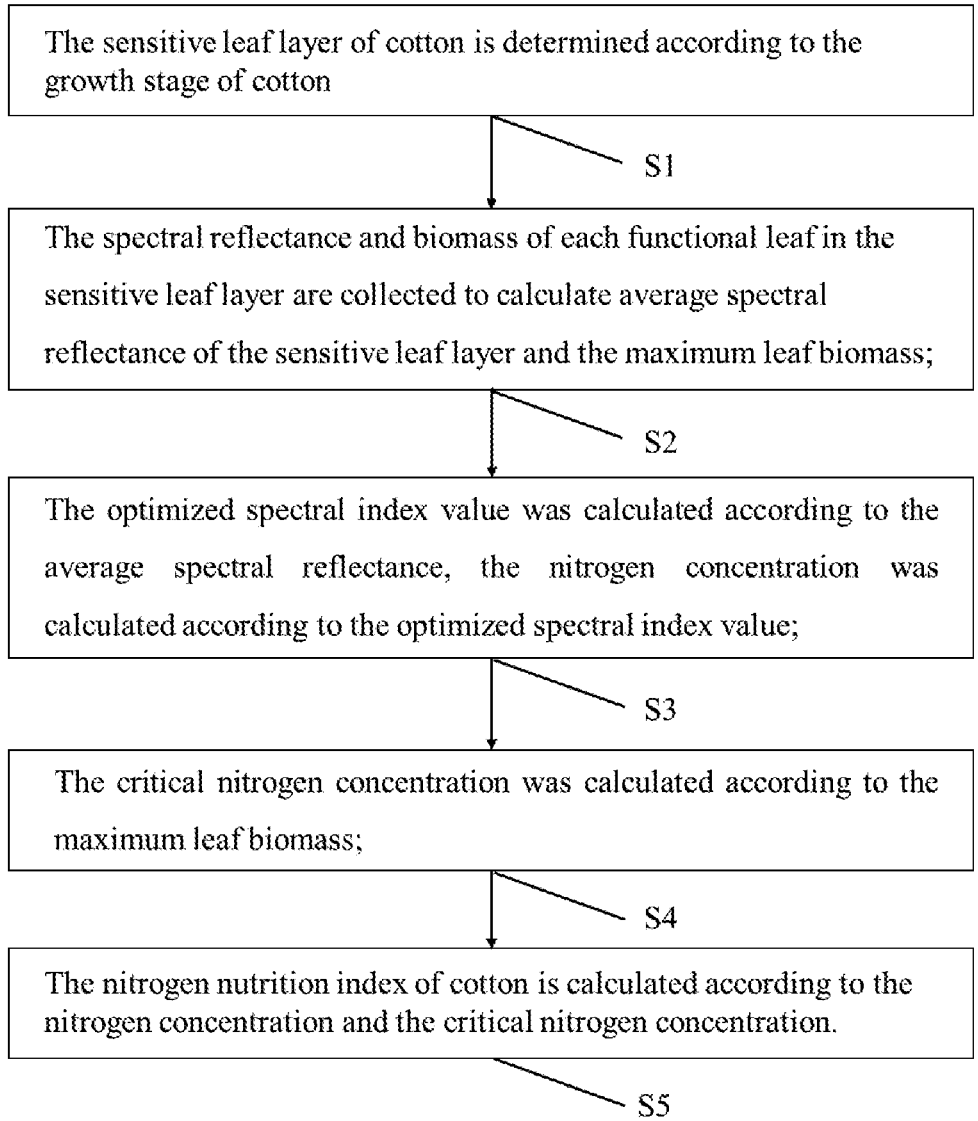
FIG. 1 is a method flowchart of the diagnosis method provided in Embodiment 1 of the present invention.

The present embodiment is used to provide a diagnostic method for drip irrigation cotton with nitrogen nutrient deficit, as shown in FIG. 1, wherein the diagnostic method comprises the following steps:

S1: The sensitive leaf layer of cotton is determined according to the growth stage of cotton;

In this embodiment, when diagnosing the nitrogen nutrient abundance of cotton, the nitrogen transport regulation of drip-irrigated cotton under different nitrogen fertilization conditions is firstly clarified, and the sensitive leaf layers corresponding to each growth stage of cotton are found, and the sensitive leaf layer can well characterize the nitrogen abundance and deficiency of cotton at this growth stage. Then, in the subsequent calculation of the nitrogen nutrient index, the relevant data of the sensitive leaf layer are directly used for calculation, which can significantly reduce the calculation amount of the nitrogen nutrient index and quickly diagnose the nitrogen nutrient abundance of drip irrigation cotton.

Figure 2:
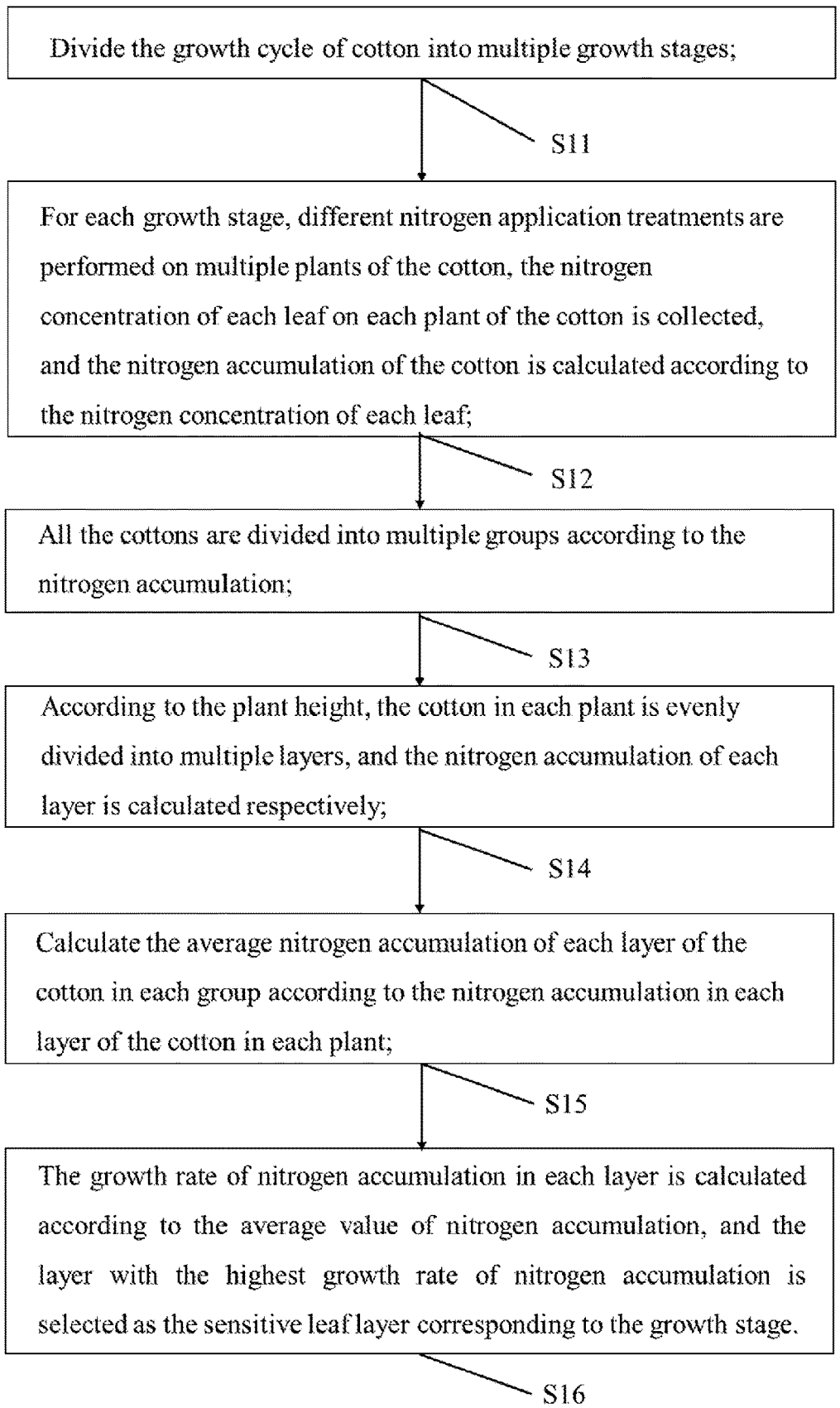
FIG. 2 is a method flowchart for determining the corresponding relationship between growth stages and sensitive leaf layers according to Embodiment 1 of the present invention.

Specifically, the diagnostic method provided in this embodiment further includes the step of determining the corresponding relationship between the growth stage and the sensitive leaf layer. As shown in FIG. 2, the step may include:

S11: Divide the growth cycle of cotton into multiple growth stages;

Specifically, in this embodiment, the growth cycle of cotton is divided into two growth stages, namely the early stage of growth and the later stage of growth. The early stage of growth includes the seedling stage and the flowering stage, and the later stage of growth includes the boll stage and the boll opening stage. Of course, the growth cycle of cotton can also be divided into other numbers of growth stages according to user requirements, and this embodiment does not limit the number of growth stages.

S12: For each growth stage, different nitrogen application treatments are performed on multiple plants of the cotton, the nitrogen concentration of each leaf on each plant of the cotton is collected, and the nitrogen accumulation of the cotton is calculated according to the nitrogen concentration of each leaf;

Different nitrogen application treatments apply different amounts of nitrogen to cotton, or apply different amounts of nitrogen fertilizer to cotton. When applying nitrogen treatment to cotton, for each nitrogen application rate, it can include multiple cottons at the same time, or only one cotton. This embodiment does not impose any restrictions on the amount of cotton corresponding to each nitrogen application rate, and only needs to ensure that different nitrogen application treatments are performed on multiple cotton plants. For example, in this embodiment, five nitrogen fertilization treatments are performed on cotton, and it is only necessary to ensure that each nitrogen fertilization treatment has at least one cotton plant, but for each nitrogen fertilization treatment, the specific cotton quantity corresponding to this nitrogen application treatment is not limited.

After different nitrogen fertilization treatments are applied to multiple cotton plants, for each cotton plant, collect the nitrogen concentration of each leaf on it, and then calculate the nitrogen accumulation of the leaf according to the nitrogen concentration of the leaf and the dry weight of the leaf. Specifically, the product of nitrogen concentration and leaf dry weight is the nitrogen accumulation of the leaf. Finally, the nitrogen accumulation of all leaves on this cotton is summed to obtain the nitrogen accumulation of cotton.

S13: All the cottons are divided into multiple groups according to the nitrogen accumulation; the larger the group number, the higher the nitrogen accumulation;

In this example, cotton is divided into three groups according to the level of nitrogen accumulation, namely the low nitrogen group with group number 1, the average group with group number 2, and the high nitrogen group with group number 3. Specifically, the nitrogen accumulation calculated under conventional fertilization conditions was used as the standard value, and the cotton with nitrogen accumulation lower than 0.7 times the standard value was classified as a low nitrogen group. Cottons whose nitrogen accumulation was between 0.7 times the standard value and 1.3 times the standard value were classified as the average group. Cottons with nitrogen accumulation higher than 1.3 times the standard value were classified as high nitrogen group, and then the cottons were divided into three groups according to the level of nitrogen accumulation. Compared with the method of grouping cotton according to the amount of nitrogen application, this grouping method can more clearly and accurately find the sensitive leaf layers that characterize the nitrogen nutrient abundance and deficiency at this growth stage.

S14: According to the plant height, the cotton in each plant is evenly divided into multiple layers, and the nitrogen accumulation of each layer is calculated respectively;

In this embodiment, the cotton is evenly divided into three layers, which are respectively recorded as the upper layer, the middle layer and the lower layer. Then, the nitrogen accumulation in the upper layer is obtained by counting the sum of the nitrogen accumulation of all leaves contained in the upper layer, and the nitrogen accumulation in the middle layer is obtained by counting the sum of the nitrogen accumulation of all leaves in the middle layer. The nitrogen accumulation in the lower layer was obtained by counting the sum of the nitrogen accumulation of all leaves contained in the lower layer. As shown in FIG. 3, (a) shows the schematic diagram of the distribution of nitrogen accumulation in each leaf layer of cotton in the early growth stage, (b) shows the schematic diagram of the distribution of nitrogen accumulation in each leaf layer of cotton in the later growth stage. In (a) and (b), the abscissa is the group number, the left ordinate is the nitrogen accumulation, and the right ordinate is the growth rate.

S15: Calculate the average nitrogen accumulation of each layer of the cotton in each group according to the nitrogen accumulation in each layer of the cotton in each plant;

The nitrogen accumulation in each layer of all cottons included in each group was summed up separately to obtain the average nitrogen accumulation in each layer of the group of cottons.

S16: The growth rate of nitrogen accumulation in each layer is calculated according to the average value of nitrogen accumulation, and the layer with the highest growth rate of nitrogen accumulation is selected as the sensitive leaf layer corresponding to the growth stage.

When calculating the growth rate, in the order of group numbers from small to large, the growth rate of nitrogen accumulation in each layer was calculated based on the average value of nitrogen accumulation in all groups. The growth rate curve is shown in FIG. 3.

In this embodiment, the change regulation of nitrogen content in the upper, middle and lower layers in the early and later growth stages was studied, and the trend of nitrogen accumulation was analyzed. In the early stage of growth, the growth rate of nitrogen accumulation in the middle-layer leaves was the fastest. Therefore, it is determined that the middle layer of leaves is the sensitive leaf layer in the early growth stage. In the later growth stage, the nitrogen accumulation of the lower leaves increased the fastest, so the lower layer of leaves was determined to be the sensitive leaf layers in the later growth stage.

Figure 4:
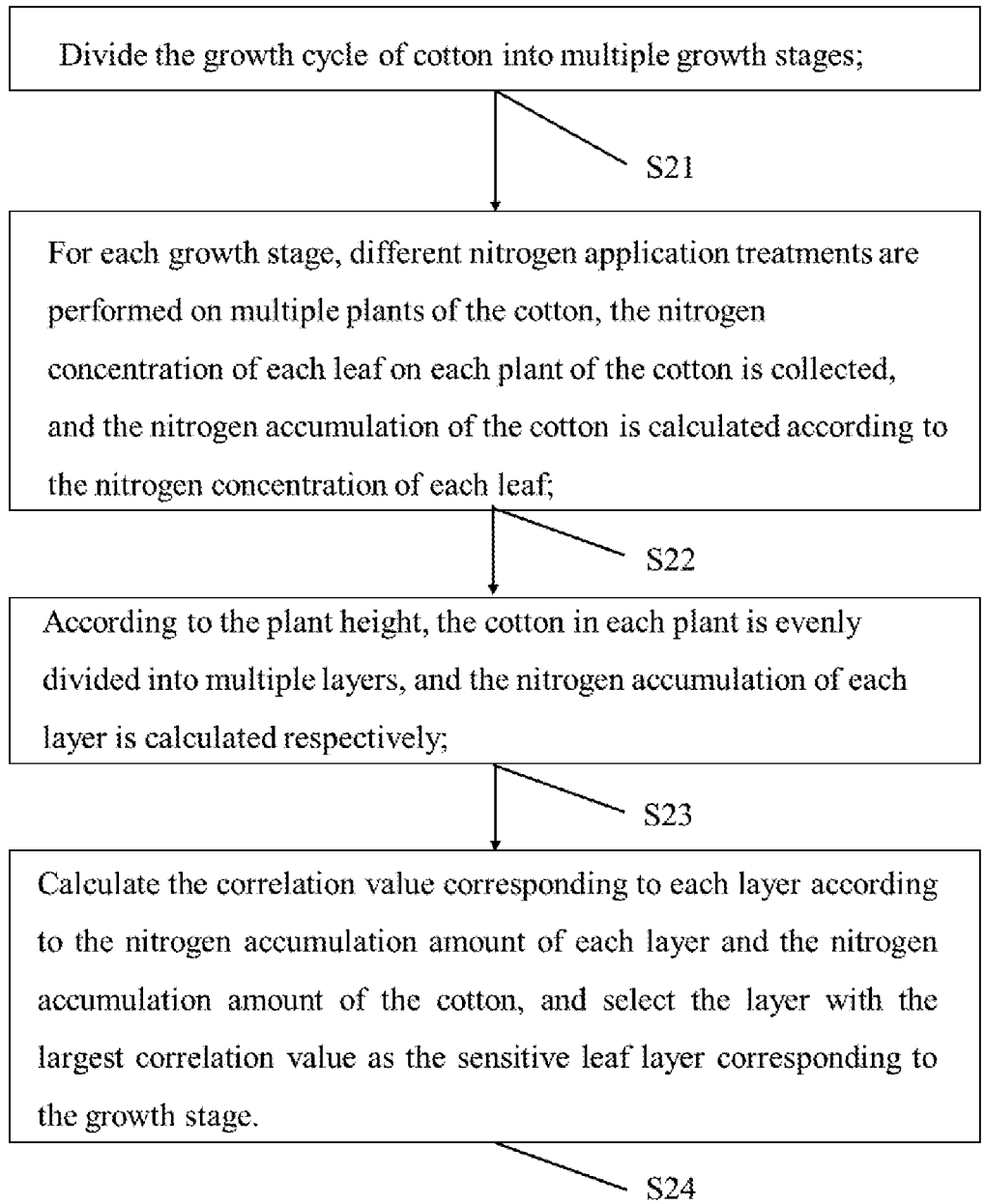
FIG. 4 is another method flowchart for determining the corresponding relationship between growth stages and sensitive leaf layers according to Embodiment 1 of the present invention.

As another optional embodiment, as shown in FIG. 4, the step of determining the corresponding relationship between the growth stage and the sensitive leaf layer may further include:

S21: Divide the growth cycle of cotton into multiple growth stages;

S22: For each growth stage, different nitrogen application treatments are performed on multiple plants of the cotton, the nitrogen concentration of each leaf on each plant of the cotton is collected, and the nitrogen accumulation of the cotton is calculated according to the nitrogen concentration of each leaf;

S23: According to the plant height, the cotton in each plant is evenly divided into multiple layers, and the nitrogen accumulation of each layer is calculated respectively;

S24: Calculate the correlation value corresponding to each layer according to the nitrogen accumulation amount of each layer and the nitrogen accumulation amount of the cotton, and select the layer with the largest correlation value as the sensitive leaf layer corresponding to the growth stage.

The nitrogen accumulation of each layer and the nitrogen accumulation of cotton are correlated in SPSS, and the correlation between the leaf nitrogen accumulation of each layer and the overall nitrogen accumulation of cotton crops is analyzed, and the corresponding correlation value of each layer is obtained, as shown in Table 1.

TABLE 1

|  | The Early Stage of Growth | The Later Stage of Growth |
| --- | --- | --- |
| Upper | 0.7043** | 0.4273 |
| Middle | 0.8153** | 0.4853 |
| Lower | 0.7860** | 0.6295* |

Note:
**represents extremely significant;
*represents significant.

By observing Table 1, the correlation between the nitrogen accumulation in the middle leaves and the overall nitrogen accumulation of cotton in the early growth stage has reached a very significant level, and the correlation value is above 0.8, which can well reflect the changes in the overall nitrogen accumulation of cotton. The correlation of the lower leaves in the later stage of growth also reached a very significant level, and the correlation value was above 0.6. Then, the sensitive leaf layer in the early stage of growth was determined as the middle layer, and the sensitive leaf layer in the later stage of growth was determined as the lower layer.

S2: Collect the spectral reflectance and biomass of each functional leaf in the sensitive leaf layer, and calculate the average spectral reflectance and the maximum leaf biomass of the sensitive leaf layer;

Use a portable spectrometer to measure the spectral reflectance of all functional leaves in the sensitive leaf layer, and calculate the average spectral reflectance of all functional leaves to obtain the average spectral reflectance. Functional leaves are leaves that are fully expanded and capable of photosynthesis to provide nutrients to crops.

S3: Calculate the optimized spectral index value according to the average spectral reflectance, and calculate the nitrogen concentration according to the optimized spectral index value;

The diagnostic method of this embodiment further includes optimizing the central wavelength of the spectral index to obtain an optimized spectral index, as shown in FIG. 5, which may include:

S31: Collect the spectral reflectance and nitrogen concentration of each functional leaf in the sensitive leaf layer of several plants of the cotton, and calculate the average spectral reflectance of the cotton according to the spectral reflectance of each functional leaf, calculate the average nitrogen concentration of the cotton according to the nitrogen concentration of each functional leaf;

S32: According to the average value of spectral reflectance and the average value of nitrogen concentration, use SPA and RF to screen multiple sensitive bands;

The spectral reflectance of each functional leaf in the sensitive leaf layer collected by the spectrometer is the information of the full band. In this embodiment, the correlation function CORREL that comes with EXCEL can be used to calculate the correlation between the average spectral reflectance and the average nitrogen concentration, and obtain the correlation between the leaf spectral data of the sensitive leaf layer and the nitrogen concentration. Then, by analyzing the correlation between the leaf spectral data of the sensitive leaf layer and nitrogen concentration, the sensitive bands were screened, and the sensitive bands could better reflect the nitrogen nutrient abundance of cotton. Specifically, SPA (continuous projection) and RF (random frog leap) methods are used to screen sensitive bands. During the screening, SPA does not limit the number of bands, and the default result shall prevail. A total of 39 sensitive bands are screened. The RF set the correlation threshold to 0.5, and a total of 16 sensitive bands were screened. The specific screening results are shown in Table 2.

TABLE 2

| Method | Number | Result |
|---|---|---|
| SPA | 39 | 1987, 648, 2103, 700, 1706, 545, 694, 759, 561, 474, 740, 1806, 540, 1893, 783, 1058, 580, 628, 481, 602, 755, 1950, 677, 454, 1806, 671, 773, 424, 761, 393, 1991, 410, 714, 433, 351, 387, 438, 730, 687 |
| RF | 16 | 1847, 1851, 734, 1058, 1955, 687, 686, 1907, 783, 688, 1818, 541, 773, 1987, 513, 1901 |

Figure 6:
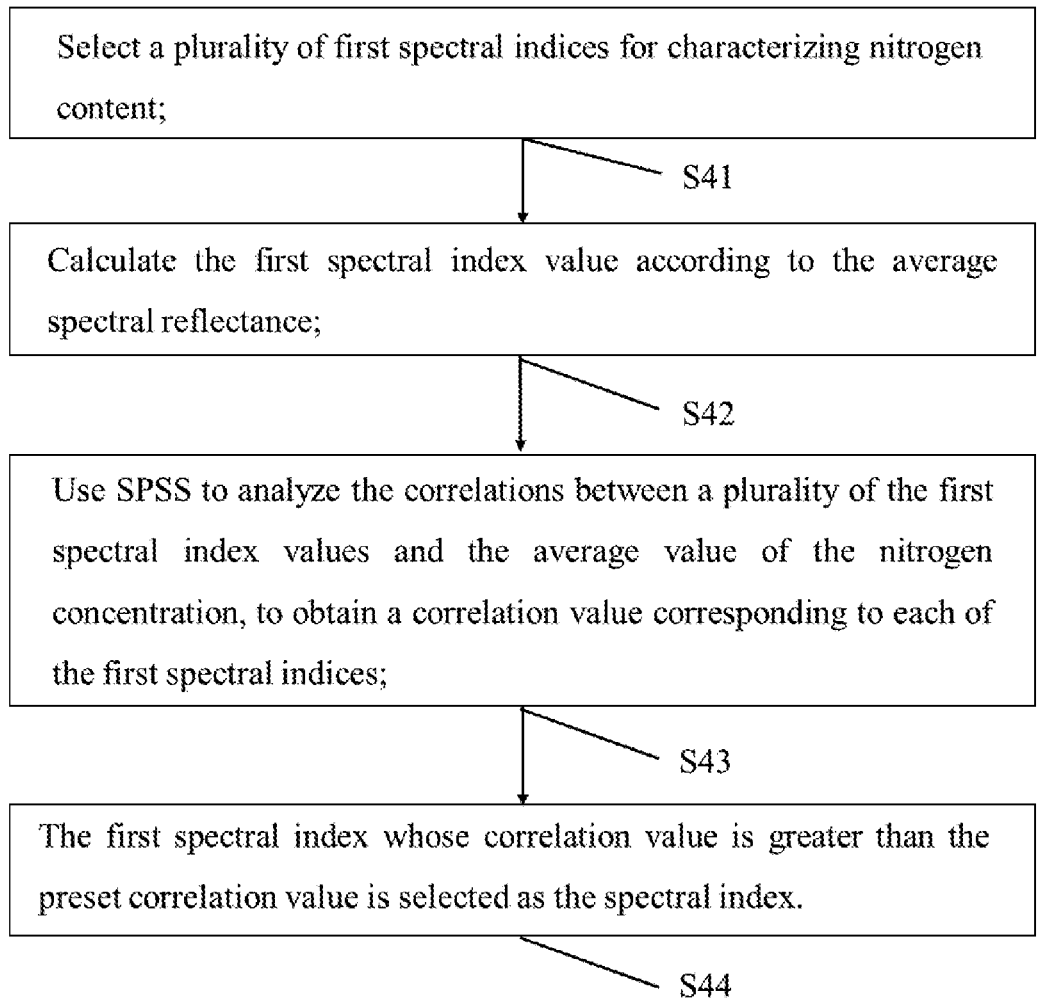
FIG. 6 is a method flowchart for selecting a spectral index according to Embodiment 1 of the present invention.

Specifically, after S32, as shown in FIG. 6, the diagnosis method further includes:

S41: Select a plurality of first spectral indices for characterizing nitrogen content;

Spectral indices have been studied in nitrogen estimation, and 14 first spectral indices can be selected to represent nitrogen content by referring to relevant data. The selected first spectral indices are shown in Table 3.

TABLE 3

| No. | Index | Abbreviation | Correlation coefficient |
|---|---|---|---|
| 1 | Simple Ratio Pigment Index | SRPI | 0.660 |
| 2 | Corrected Red-Edge Single Ratio Index | mSR705 | 0.810* |
| 3 | Corrected Red-Edge Normalization Index | mNDVI 705 | 0.696 |
| 4 | Normalized Pigment Chlorophyll Index | NPCI | 0.334 |
| 5 | Red-Edge Normalized Index | RENDVI | 0.766 |
| 6 | Ratio Index | RI-1dB | 0.790* |
| 7 | vogelmann Red-Edge Index | VOG | 0.770 |
| 8 | Bimodal Canopy Nitrogen Index | DCNI | 0.822** |
| 9 | Photochemical Reflectance Index | PRI | 0.726 |
| 10 | Ratio Vegetation Index | RVI | −0.844* |
| 11 | Normalized Vegetation Index | NDVI | 0.415 |
| 12 | Red-Edge Spectral Ratio Vegetation Index | VOG3 | −0.682 |
| 13 | Red-Edge Normalized Vegetation Index | ND705 | 0.766* |
| 14 | Nitrogen Reflectance Index | NRI | −0.718 |

S42: Calculate the first spectral index value according to the average spectral reflectance;

For each first spectral index, according to the calculation formula of the first spectral index, select the average reflectance of each wavelength band corresponding to the first spectral index from the average spectral reflectance obtained in Si, and bring it into the calculation formula of the first spectral index to obtain the value of the first spectral index.

S43: Use SPSS to respectively analyze the correlations between a plurality of the first spectral index values and the average value of the nitrogen concentration, to obtain a correlation value corresponding to each of the first spectral indices;

The correlation values corresponding to each first spectral index are shown in Table 3.

S44: Select the first spectral index whose correlation value is greater than the preset correlation value as the spectral index.

In this embodiment, five first spectral indices are specifically selected as spectral indices, and then the central wavelength of the spectral indices is optimized by S34 to obtain the optimized spectral indices.

S33: The central wavelength of the spectral index is optimized by using the sensitive band to obtain the optimized spectral index.

Since most of the existing spectral indices are established for the study of wheat, rice and other cereal crops, the planting pattern and environment of cotton in Xinjiang are very different from those of wheat, rice and other cereal crops, and the spectral indices applicable to cereal crops are not necessarily applicable to cotton. Therefore, after obtaining the spectral index that can better characterize the nitrogen content, the central wavelength of the spectral index was optimized using the sensitive band. The optimization results are shown in Table 4.

TABLE 4

| Abbreviation | Optimal Center Wavelength | | | $R^2$ | RMSE |
|---|---|---|---|---|---|
| | R1 | R2 | R3 | | |
| SPA-mSR705 | 755 | 445 | 708 | 0.679 | 4.53 |
| SPA-RI-1dB | 738 | 719 | | 0.611 | 4.87 |
| SPA-DCNI | 725 | 706 | 677 | 0.683 | 4.46 |
| SPA-RVI | 789 | 677 | | 0.541 | 5.02 |
| SPA-ND705 | 755 | 708 | | 0.636 | 4.55 |
| RF-mSR705 | 750 | 448 | 707 | 0.659 | 4.59 |
| RF-RI-1dB | 736 | 723 | | 0.642 | 4.57 |
| RF-DCNI | 723 | 705 | 673 | 0.707 | 3.86 |
| RF-RVI | 788 | 673 | | 0.584 | 4.97 |
| RF-ND705 | 750 | 707 | | 0.638 | 4.51 |

Note:
R1, R2 and R3 are the optimal central wavelengths that constitute the spectral index, respectively.

When optimizing the central wavelength of the spectral index, the original central wavelength is directly replaced with the value of the sensitive band closest to the central wavelength. Taking the modified red-edge single ratio index mSR705 as an example, when the central wavelength of this spectral index is optimized, the original central wavelengths of the spectral index are R750, R445, and R705, respectively, representing the central wavelength of red-edge, blue-edge, and red-light. However, the central wavebands screened by continuous projection are R755, R445, and R708. Therefore, the original central wavelength is directly replaced by the screened sensitive waveband, and the new central wavelength is used to construct SPA-mSR705 to complete the optimization of the original spectral index, to improve the estimation accuracy of the spectral index.

This embodiment further includes establishing a nitrogen estimation linear model between the optimized spectral index and the nitrogen concentration after the spectral index is optimized by the central wavelength using the sensitive band to obtain the optimized spectral index. The nitrogen concentration is then calculated from the spectral reflectance average using this nitrogen estimation linear model.

When establishing a linear model, first calculate the optimal spectral index value based on the average spectral reflectance, and then for each optimal spectral index, perform linear fitting on the optimal spectral index value and the average nitrogen concentration to obtain the optimal spectral index and nitrogen concentration. The relationship between the optimized spectral index and nitrogen concentration linear model is obtained. The resulting linear models for nitrogen estimation are shown in Table 5.

TABLE 5

| Index | Equation | $R^2$ | RMSE |
|---|---|---|---|
| SPA-mSR705 | Y = 8.72X − 10.351 | 0.659 | 3.73 |
| SPA-RI-1dB | Y = 32.016X − 13.283 | 0.601 | 4.57 |
| SPA-DCNI | Y = 1.868X + 18.515 | 0.673 | 4.56 |
| SPA-RVI | Y = 46.58X − 2.238 | 0.521 | 4.92 |
| SPA-ND705 | Y = 70.772X − 5.8457 | 0.616 | 4.45 |
| RF-mSR705 | Y = 7.631X − 9.176 | 0.402 | 4.89 |
| RF-RI-1dB | Y = 34.13X − 14.752 | 0.542 | 4.77 |
| RF-DCNI | Y = 2.87X + 9.331 | 0.607 | 4.66 |
| RF-RVI | Y = 57.9X − 12.437 | 0.584 | 4.87 |
| RF-ND705 | Y = 76.532X − 7.788 | 0.538 | 4.11 |

Note:
Y is the nitrogen concentration, X is the optimized spectral index value.

Furthermore, using the nitrogen estimation linear model in Table 5, the nitrogen concentration of cotton was calculated according to the average spectral reflectance. In the actual calculation, the optimal nitrogen estimation linear model can be selected, for the optimized spectral index corresponding to this nitrogen estimation linear model, the optimized spectral index value is calculated according to the average spectral reflectance to obtain the most accurate nitrogen concentration.

In this embodiment, the sensitive band is first screened, and the spectral index that can characterize the nitrogen content is selected, and then the spectral index is optimized by using the sensitive band to obtain the optimized spectral index, which can be better applied to the plant of drip irrigation cotton, and the cotton can be calculated more accurately nitrogen concentration.

S4: Calculate the critical nitrogen concentration according to the maximum leaf biomass;

Calculate the critical nitrogen concentration according to the following formula:

$$N_c = 6.89 \times W^{-0.22}; \qquad (1)$$

Wherein, $N_c$ is the critical nitrogen concentration; W is the maximum leaf biomass.

Specifically, the method for determining the critical nitrogen concentration calculation formula is as follows: under the five nitrogen application treatments shown in Table 6, determine the maximum leaf biomass and nitrogen concentration values of Xinluzao 53, and then fit the maximum leaf biomass and nitrogen concentration values according to $N_c = \alpha \times W^{-b}$, using the data in Table 6 to determine the parameters a and b, so as to determine the specific critical nitrogen concentration calculation formula. The accuracy of the formula for calculating the critical nitrogen concentration obtained by this method is $R^2 = 0.87$.

TABLE 6

| Year | Variety | Treatment | Ym/(t · hm$^{-2}$) | N % |
|---|---|---|---|---|
| 2019 | | N0 | 23.05 | 3.27 |
| | | N1 | 25.61 | 3.38 |
| | Xinluzao 53 | N2 | 27.29 | 3.44 |
| | | N3 | 27.57 | 3.53 |
| | | N4 | 26.89 | 3.46 |
| 2020 | | N0 | 20.34 | 3.26 |
| | | N1 | 22.33 | 3.27 |
| | Xinluzao 53 | N2 | 25.05 | 3.39 |
| | | N3 | 27.88 | 3.49 |
| | | N4 | 26.00 | 3.45 |

S5: The calculation of the nitrogen nutrient index of the cotton according to the nitrogen concentration and the critical nitrogen concentration specifically includes:

$$NNI = \frac{N}{N_c}; \qquad (2)$$

In formula 2, NNI is nitrogen nutrition index; N is nitrogen concentration; $N_c$ is critical nitrogen concentration; NNI is equal to 1, indicating that the nitrogen nutrition of the cotton is in the best state; NNI is less than 1, indicating that the nitrogen nutrition of the cotton is insufficient; NNI is greater than 1, indicating the nitrogen excess of the cotton.

Rapid and accurate diagnosis of nitrogen nutrition is the key to optimizing nitrogen supply to crops. Due to the typical vertical heterogeneity of nitrogen distribution in cotton plants, before the "symptom" of nitrogen deficiency in the canopy, cotton is already in the "middle and later stage" of nitrogen deficiency, which seriously affects cotton growth and yield formation. The diagnostic method provided in this embodiment can identify the nitrogen nutrient abundance and deficiency in cotton production at an early stage, intuitively and quickly provide the judgment of the abundance or lack of nitrogen nutrient in drip irrigation cotton, and adjust fertilization in time according to the nutrient abundance and deficiency. so as to achieve rational application of nitrogen fertilizer. The traditional spectral vertical monitoring method is difficult to detect the nutritional status of different leaf layers. Therefore, in this embodiment, selecting the sensitive leaf layer that is rich in nitrogen nutrient and combining it with the nitrogen nutrient index to diagnose the nitrogen nutrition status of the sensitive leaf layer, it provides technical support for the early diagnosis of nitrogen deficiency in cotton.

Embodiment 2

Figure 7:
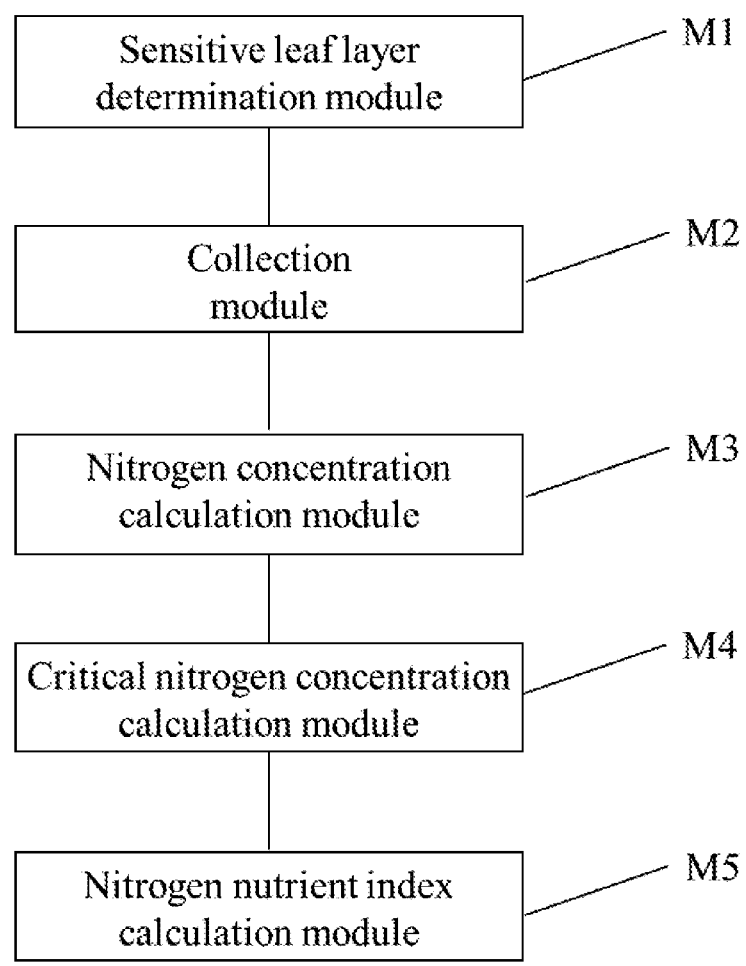
FIG. 7 is a structural block diagram of a diagnosis system provided by Embodiment 2 of the present invention.

This embodiment is used to provide a system for drip irrigation cotton with nitrogen nutrient deficit, as shown in FIG. 7, wherein the diagnosis system comprises:

A sensitive leaf layer determination module M1, used for determining the sensitive leaf layer of the cotton according to the growth stage of the cotton;

A collection module M2, configured to collect the spectral reflectance and biomass of each functional leaf in the sensitive leaf layer, and calculate the average spectral reflectance and the maximum leaf biomass of the sensitive leaf layer;

A nitrogen concentration calculation module M3, configured to calculate an optimized spectral index value according to the average spectral reflectance, and to calculate a nitrogen concentration according to the optimized spectral index value;

A critical nitrogen concentration calculation module M4, configured to calculate the critical nitrogen concentration according to the maximum leaf biomass;

A nitrogen nutrient index calculation module M5, used for calculating the nitrogen nutrient index of the cotton according to the nitrogen concentration and the critical nitrogen concentration; the nitrogen nutrient index is used to characterize the nitrogen nutrient abundance of the cotton.

The various embodiments in this specification are described in a progressive manner, and each embodiment focuses on the differences from other embodiments, and the same and similar parts between the various embodiments can be referred to each other. For the system disclosed in the embodiment, since it corresponds to the method disclosed in the embodiment, the description is relatively simple, and the relevant part can be referred to the description of the method.

The principles and implementations of the present invention are described herein using specific embodiments. The descriptions of the above embodiments are only used to help understand the method and the core idea of the present invention; meanwhile, for those skilled in the art, according to the idea of the present invention, there will be changes in the specific embodiments and application scopes. In conclusion, the contents of this specification should not be construed as limiting the present invention.

The invention claimed is:

1. A diagnostic method for drip irrigation cotton with nitrogen nutrient deficit, wherein the diagnostic method comprises the following steps: determining sensitive leaf layer of cotton according to the growth stage of cotton; collecting spectral reflectance and biomass of each functional leaf in the sensitive leaf layer, calculating average spectral reflectance of the sensitive leaf layer and maximum leaf biomass; calculating optimized spectral index value according to the average spectral reflectance, calculating nitrogen concentration according to the optimized spectral index value; calculating critical nitrogen concentration according to the maximum leaf biomass; calculating nitrogen nutrition index of the cotton according to the nitrogen concentration and the critical nitrogen concentration, using the nitrogen nutrition index to characterize the abundance and deficiency of nitrogen nutrition in the cotton.

2. The diagnostic method for drip irrigation cotton with nitrogen nutrient deficit according to claim 1, wherein before determining the sensitive leaf layer of the cotton according to the growth stage of the cotton, the diagnostic method also includes the step of determining the corresponding relationship between the growth stage and the sensitive leaf layer, which specifically includes: dividing the growth cycle of cotton into multiple growth stages; Efor each growth stage, different nitrogen application treatments are performed on multiple plants of the cotton, collecting the nitrogen concentration of each leaf on each plant of the cotton is collected, and the calculating nitrogen accumulation of the cotton is calculated according to the nitrogen concentration of each leaf; AH dividing the cottons are divided into multiple groups according to the nitrogen accumulation; the larger the group number, the higher the nitrogen accumulation; According to the plant height, dividing the cotton in each plant is evenly divided into multiple layers according to the plant height, and calculating the nitrogen accumulation of each layer is calculated respectively; Calculate the calculating average nitrogen accumulation of each layer of the cotton in each group according to the nitrogen accumulation in each layer of the cotton in each plant; calculating growth rate of nitrogen accumulation in each layer is calculated according to the average value of nitrogen accumulation, and selecting the layer with the highest growth rate of nitrogen accumulation is selected as the sensitive leaf layer corresponding to the growth stage.

3. The diagnostic method for drip irrigation cotton with nitrogen nutrient deficit according to claim 1, wherein before determining the sensitive leaf layer of the cotton according to the growth stage of the cotton, the diagnostic method also includes the step of determining the corresponding relationship between the growth stage and the sensitive leaf layer, which specifically includes: dividing the growth cycle of cotton into multiple growth stages; for each growth stage, different nitrogen application treatments are performed on multiple plants of the cotton, collecting the nitrogen concentration of each leaf on each plant of the cotton is collected, and calculating the nitrogen accumulation of the cotton is calculated according to the nitrogen concentration of each leaf; According to the plant height, dividing the cotton in each plant is evenly divided into multiple layers according to the plant height, and calculating the nitrogen accumulation of each layer is calculated respectively; calculating the correlation value corresponding to each layer according to the nitrogen accumulation amount of each layer and the nitrogen accumulation amount of the cotton, and select selecting the layer with the largest correlation value as the sensitive leaf layer corresponding to the growth stage.

4. The diagnostic method for drip irrigation cotton with nitrogen nutrient deficit according to claim 2, wherein the calculating the nitrogen accumulation of the cotton according to the nitrogen concentration of each leaf specifically comprises: calculating the nitrogen accumulation of the leaves according to the nitrogen concentration of the leaves and the dry weight of the leaves; summing the nitrogen accumulation of all the leaves was summed to obtain the nitrogen accumulation of the cotton.

5. The diagnostic method for drip irrigation cotton with nitrogen nutrient deficit according to claim 1, wherein the diagnostic method also includes optimizing the central wavelength of the spectral index to obtain the optimized spectral index, which specifically includes: Collect collecting the spectral reflectance and nitrogen concentration of each functional leaf in the sensitive leaf layer of several plants of the cotton, and calculate calculating the average spectral reflectance of the cotton according to the spectral reflectance of each functional leaf, calculate calculating the average nitrogen concentration of the cotton according to the nitrogen concentration of each functional leaf; According to the average value of spectral reflectance and the average value of nitrogen concentration, use using SPA and RF to screen multiple sensitive bands according to the average value of spectral reflectance and the average value of nitrogen concentration; obtaining the optimized spectral index by optimizing the central wavelength of the spectral index by using the sensitive band.

6. The diagnostic method for drip irrigation cotton with nitrogen nutrient deficit according to claim 5, wherein after using the SPA and the RF to screen a plurality of sensitive bands according to the correlation, the diagnostic method further comprises: selecting a plurality of first spectral indices for characterizing nitrogen content; calculating the first spectral index value according to the average spectral reflectance; using SPSS to analyze the correlations between a plurality of the first spectral index values and the average value of the nitrogen concentration, to obtain obtaining a correlation value corresponding to each of the first spectral indices; selecting the first spectral index whose correlation value is greater than the preset correlation value as the spectral index.

7. The diagnostic method for drip irrigation cotton with nitrogen nutrient deficit according to claim 5, wherein after obtaining the optimized spectral index, the diagnostic method further comprises: calculating the optimized spectral index value according to the average spectral reflectance; for each of the optimized spectral indices, linear fitting is performed on the optimized spectral index value and the average value of the nitrogen concentration to obtain, obtaining a relationship between the optimized spectral index and the nitrogen concentration.

8. The diagnostic method for drip irrigation cotton with nitrogen nutrient deficit according to claim 1, wherein calculating the critical nitrogen concentration calculation according to the maximum leaf biomass specifically comprises:

$$N_c = 6.89 \times W^{-0.22};$$

Wherein, $N_c$ is the critical nitrogen concentration; W is the maximum leaf biomass.

9. The diagnostic method for drip irrigation cotton with nitrogen nutrient deficit according to claim 1, wherein the calculation of calculating the nitrogen nutrient index of the cotton according to the nitrogen concentration and the critical nitrogen concentration specifically includes:

$$NNI = \frac{N}{N_c};$$

Wherein, NNI is nitrogen nutrition index; N is nitrogen concentration; Nis critical nitrogen concentration; NNI is equal to 1, indicating that the nitrogen nutrition of the cotton is in the best state; NNI is less than 1, indicating that the nitrogen nutrition of the cotton is insufficient; NNI is greater than 1, indicating the nitrogen excess of the cotton.

10. A system for drip irrigation cotton with nitrogen nutrient deficit, wherein the diagnosis system comprises: a sensitive leaf layer determination module, configured to determine the sensitive leaf layer of the cotton according to the growth stage of the cotton; a collection module, configured to collect the spectral reflectance and biomass of each functional leaf in the sensitive leaf layer, and calculating the average spectral reflectance and the maximum leaf biomass of the sensitive leaf layer; a nitrogen concentration calculation module, configured to calculate an optimized spectral index value according to the average spectral reflectance, and calculating a nitrogen concentration according to the optimized spectral index value; a critical nitrogen concentration calculation module, configured to calculate the critical nitrogen concentration according to the maximum leaf biomass; a nitrogen nutrient index calculation module, configured to calculate the nitrogen nutrient index of the cotton according to the nitrogen concentration and the critical nitrogen concentration; using the nitrogen nutrient index to characterize the nitrogen nutrient abundance of the cotton.

* * * * *